United States Patent [19]

Garnier et al.

[11] Patent Number: 5,058,127

[45] Date of Patent: Oct. 15, 1991

[54] BOTTOM DISCHARGE COLD CRUCIBLE

[75] Inventors: Marcel Garnier, St. Martin d'Uriage; Isabelle Gleizes, St. Martin d'Hères; Patrick Paillere, Ugine; Pierre Vernay, Meylan, all of France

[73] Assignee: Compagnie Europeenne du Zirconium Cezus, Courbevoie, France

[21] Appl. No.: 509,189

[22] Filed: Apr. 16, 1990

[30] Foreign Application Priority Data

May 19, 1989 [FR] France .................................. 89 07027

[51] Int. Cl.$^5$ ............................................. H05B 6/22
[52] U.S. Cl. ...................................... 373/157; 373/83; 373/142
[58] Field of Search ................. 373/83, 142, 156, 157, 373/158

[56] References Cited

U.S. PATENT DOCUMENTS 3,461,215  8/1969  Reboux .................................. 373/158
3,531,574  9/1970  Sterling et al. ...................... 373/158
3,709,678  1/1973  Helary et al. ........................ 373/158

Primary Examiner—Bruce A. Reynolds
Assistant Examiner—Tu Hoang
Attorney, Agent, or Firm—Dennison, Meserole, Pollack & Scheiner

[57] ABSTRACT

The present invention relates to a cold crucible adapted to be discharged through the bottom. The crucible consists of a conductive wall consisting of a plurality of longitudinal hollow segments which are electrically insulated at least partially from one another and which are by virtue of the longitudinal hollows adapted to be traversed internally by a cooling fluid and which crucible is adapted to be placed inside an inductor and in which the wall is provided in its bottom part with an aperture inside which there is a removable occluding member, formed of segments which member is cooled like the wall of the crucible. The crucible is used in the processing of materials of high purity which can be recovered in the liquid state in a convenient complete and rapid manner.

3 Claims, 1 Drawing Sheet

BOTTOM DISCHARGE COLD CRUCIBLE

The present invention relates to a cold crucible adapted to be emptied through the bottom.

The processing of materials with a very high degree of purity, or reactive materials and of materials with a very high melting point generally requires them to pass through the liquid state and to be maintained in this state for a sufficiently long time to achieve homogenisation of the liquid vis-a-vis the various constituents or the temperature or even to allow chemical reactions to take place within the liquid. To do this, it is important that a turbulent agitation should keep the liquid in motion while not being capable of reacting on any of the material walls generally vital to containment of the liquid.

The solution employed in order to carry out this processing more often than not resides in using an induction-heated cold crucible. Such a crucible consists of a conductive wall, generally of copper, made up from a plurality of hollow longitudinal segments which are electrically insulated from one another and which are traversed internally by a circulation of cooling fluid which makes it possible to maintain their surface area in contact with the liquid metal at a temperature generally close to or less than 300° C. This crucible is placed inside an inductor which is supplied with alternating current which creates induced currents in the segments, currents which are completed as they pass through the inner wall of the crucible and in which they create a magnetic field.

Any electrically conductive material placed in such a crucible becomes the seat of induced currents which make it possible to heat it to melting point while at the same time agitating it. These crucibles can function in two ways:

on the one hand, in levitation. In fact, the internal walls of the crucible are generally downwardly conical so that the cross-section of the latter is smaller at the bottom than it is at the top. Thus, in principle, the product of the magnetic field multiplied by the cross-section of the crucible is substantially constant on the axis of the crucible. The result therefore is a magnetic field which increases strongly from the top to the bottom of the crucible. This configuration is perfectly well suited to levitation because the forces of repulsion induced into an electro-conductive material placed in the crucible are very strong in the bottom part of the material and decrease towards the upper part. A liquid can therefore be maintained in stable levitation in such a crucible. With the crucible cold, any interruption in power is not a danger because the liquid expanding in the crucible, functioning as an actual ingot mould, becomes solidified. The return of voltage to the inductor makes it possible to fuse the material again and to resume levitation. In the levitation state, the material which can be placed in contact with a controlled atmosphere suffers no damage. Furthermore, the electromagnetic forces induce a turbulent agitation in the liquid. The processing conditions adapted to obtain a high level of purity can therefore be satisfied;

firstly as an auto-crucible. In fact, in this same type of crucible, when the mass of liquid material becomes excessive, the electromagnetic forces can no longer balance the weight forces and the contact between the material and the wall of the crucible becomes unavoidable. However, there is no deterioration of the material because when it comes to the liquid state in contact with the wall, there is localised solidification. The liquid material is then contained in a wall which consists of a solid film constituted by the material itself. Furthermore, the contact between the solid material and the crucible is cold: therefore, there is neither pollution nor reaction. Therefore, it is likewise possible to process under a high level of purity the liquid material agitated by the magnetic field.

In both cases, there is no temperature limit. In levitation, the processing takes place without contact and thermal exchange between the material and the crucible is carried out by radiation: therefore, they remain very limited.

In the auto-crucible, it is sufficient to provide for powerful cooling of the segments of the crucible in order to maintain a crust of solid material on the internal wall.

Even with batch temperatures close to 3000° C., water is adequate as a fluid for cooling the crucible.

Once the material in the said crucibles has been treated, it is then necessary to recover it. This recovery operation has to be carried out under conditions such that they do not give rise to any pollution in order not to lose the advantages gained during processing. It is also necessary that this recovery should be rapid, convenient and complete.

Many methods of recovery have been suggested:

For example, in a very elementary manner, it is possible to leave the material to cool in the crucible and then to remove it form the mould; but this operation is not very convenient and does not make it possible to obtain a product of a specific form: therefore, one is obliged to melt it again.

In U.S. Pat. No. 4,738,713, the liquid material is poured from the crucible into a mould. As the crucible has only a single aperture which is disposed in the upper part of the crucible, recovery can only take place by the crucible being tilted. Unless some sophisticated equipment is available which makes it possible to insulate the crucible and the mould from the atmosphere, this operation is generally carried out in the air and inevitably gives rise to pollution of the material by oxidation or nitridaton. Furthermore, the tilting process is not convenient because to avoid the crucible becoming detached from its cooling water and electrical current supplies, it is necessary to resort to a very complicated mechanical system.

It is also possible to envisage, as in the case of French Patent 2561761, equipping the crucible with a lateral discharge pourer, but this has the drawback on the one hand of requiring modifications to segments to ensure its passage and also of not allowing complete emptying of the crucible. Furthermore, with materials which have a high melting point, this pourer runs the risk of becoming readily clogged if it is not equipped with suitable heating means.

This is why the Applicants, conscious of the difficulties which these recovery methods might present, have sought and found a discharge method which does not result in pollution and hwich is at once convenient, complete and rapid.

The consequence is the invention which consists of a cold crucible adapted to be emptied through the bottom and consisting of a wall constituted by several longitudinal segments which are hollow, at least partially electrically insulated from one another, and traversed internally by a cooling fluid and disposed inside an inductor and in which the said wall is provided at its bottom part with an aperture, the said invention being characterised in that a removable segmented and cooled occluding means is disposed inside the said aperture.

Thus, all in all, the invention resides in placing in the bottom aperture of the crucible an occluding means which is designed like a crucible of small size, that is to say one which has hollow segments insulated elecrically from one another and traversed internally by a cooling fluid. These segments are not extended over the entire horizontal cross-section of the occluding means and allow space for a central aperture of a diameter generally less than 3 mm, an aperture which may possibly be closed with an electrically insulated material.

When current is passing through the inductor, the induced currents appear in the crucible. In the bottom part of the crucible, these induced currents create a magnetic field which is the source of new currents which are induced into the occluding means placed in the aperture. In the "closed" position, there is therefore no material hole nor any magenetic hole in the bottom part of the crucible which behaves like a crucible consisting of a single piece. Levitation is therefore possible.

To allow the flow of the liquid material which is maintained in levitation, it is sufficient rapidly to eliminate the small crucible which closes the main crucible. The magnetic field then has a fault on the axis in the bottom part of the liquid which it can no longer withstand. Then, the flow take place through the aperture which is thus created.

In the case of the auto-crucible, the procedure is the same except that ablation of the small crucible creates a magnetic hole but the crust of solidified metal prevents the liquid from flowing. There are then two possible ways of releasing the material hole:

either an increase in power in the inductor which is reflected in two possible effects: firstly, a rise in the temeprature of the liquid accompanied by an increase in the intensity of agitation, conditions propitious to the remelting of the solid crust in the zone where the wall of the cooled crucible no longer discharges the heat; on the other hand, the edges of the orifice behave as a magnetic field concentrator which, when there is an increase in power, locally increases the Joule's effect developed in the material and encourages its fusion;

or the use of an associated inductor placed at the base of the main crucible designed for the purpose and the energising of which causes fusion of the solid crust forming the orifice and allows a flow.

Preferably, the number of segments of the occluding means is less than or equal to the number of segments of the crucible and is in any case equal to two.

Furthermore, it is preferable to give to the walls of the aperture and of the occluding means an upwardly concical shape in order to facilitate release of the occluding means.

This release is achieved by any mechanical means connected to the occluding means and which makes it possible successively to obtain a vertically downwards movement and then a translatory movement to the right or to the left to leave no obstacle to the passage of the material which is flowing. Such an occluding means may be used for a large number of processing operations.

The invention will be more clearly understood with the aid of the attached sheet of drawings in which the crucible 1, is for purposes of environmental placement, shown within an induction heating coil 9.

Figure 1:
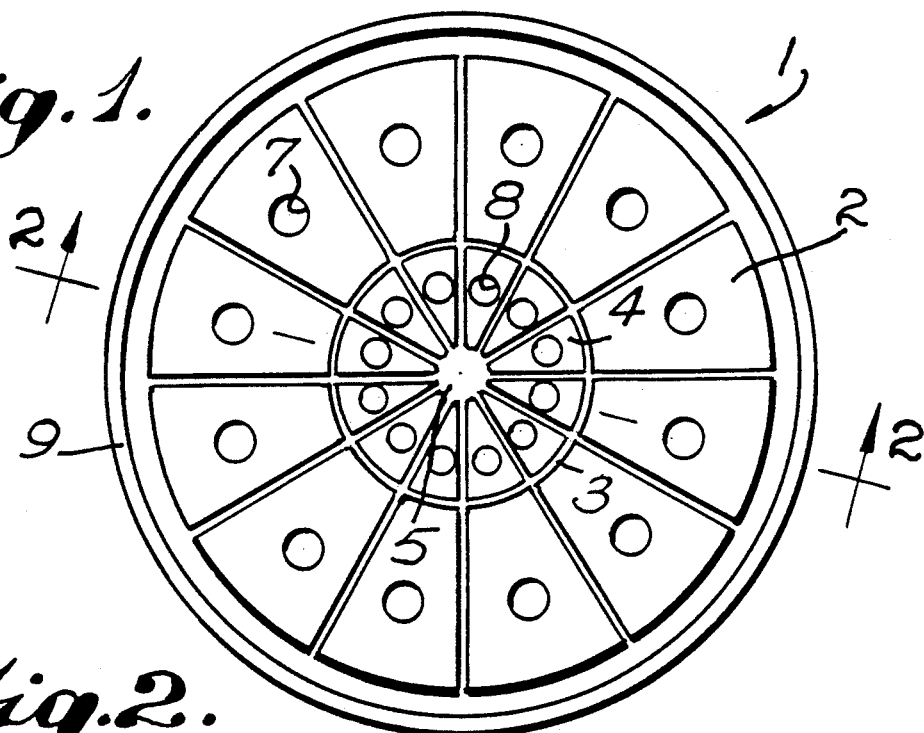
FIG. 1 is a plan view of a crucible according to the invention.

In greater detail, FIG. 1 shows the crucible 1 divided into twelve hollow and cooled segments 2 surrounding an aperture 3 in which there is an occluding means 4 likewise consisting of twelve hollow and cooled segments which do not occupy the entire cross-section of the aperture and which allow space for a circular hole 5.

Figure 2:
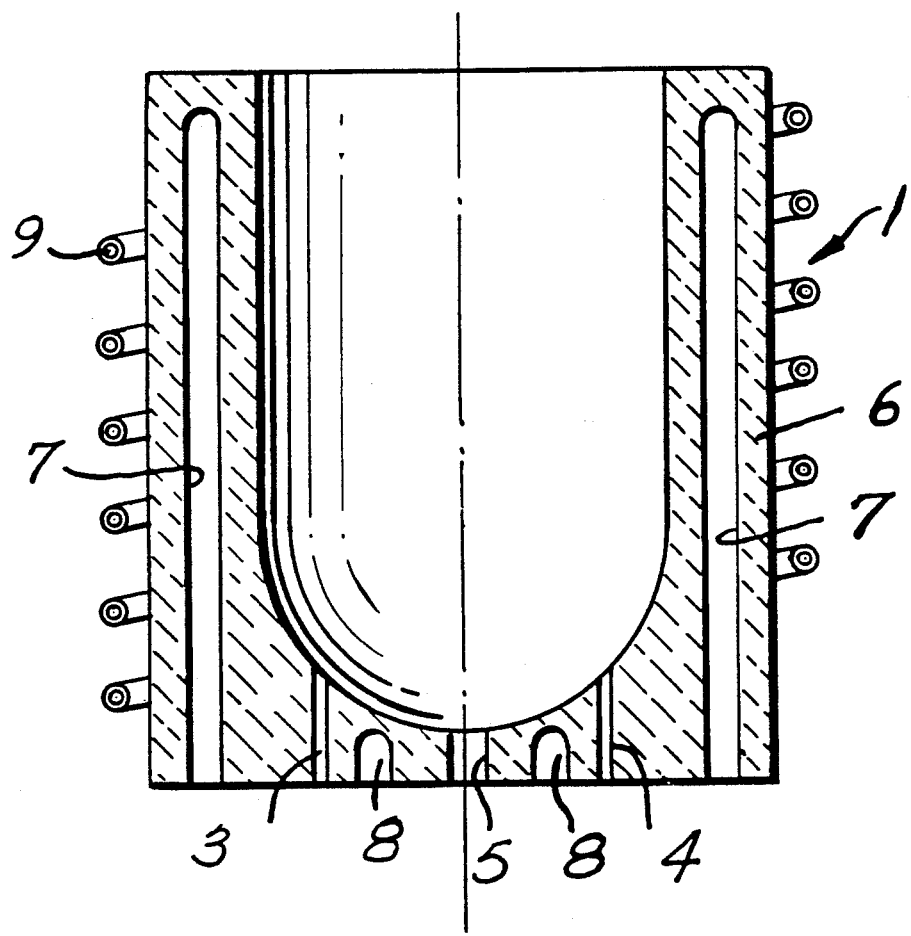
FIG. 2 is a vertical section through the same crucible.

In FIG. 2, the crucible 1 which has a lateral wall 6 provided at the bottom and according to its vertical axis with an aperture 3 in which is the removable occluding means consisting of hollow and cooled segments 4 bounded toward the centre by the hole. This crucible, in use, is surrounded by an inductor 9 and the segments are cooled by introduction of a cooling fluid, such as water, into longitudinal bores 7 and 8. These longitudinal bores may be utilized as in above cited U.S. Pat. No. 4,738,713 to provide the cooling circuits; these elements are not shown.

In operation, the elements of the material to be treated having been introduced into the crucible, the inductor is supplied with alternating current in such a way as to melt the said materials, to stir them and possibly to cause them to react. At the end of reaction the material being homogeneous and completely melted, the occluding means is rapidly displaced, first vertically as shown by the downwardly directed arrows in FIG. 2 and then laterally in order to allow the material to flow.

The flow of material may be regulated by affecting the strength of the current which supplies the inductor.

Indeed, if a very high current intensity is maintained, the material may remain in levitation; on the other hand, if this intensity is progressively lowered, then levitation is progressively suppressed and the rate of flow can be regularly increased.

The invention may be illustrated by means of the following examples of application:

EXAMPLE 1

A crucible of 100 mm diameter consisting of 12 longitudinal hollow segments which are electrically insulated from one another but which are traversed internally by a cooling fluid and which are placed inside an inductor supplied with alternating current of a frequency of 15 kHz and a current power of 80 kW and the bottom of which is provided with an aperture of 16 mm diameter, was equipped with an occluding means of a diameter close to that of the aperture, being 40 mm high and consisting of 4 insulated and cooled segments.

In this crucible, 400 g of nickel were melted, being then discharged through the bottom in 3 seconds, there being rapidly imprinted on the occluding means a downwards vertical movement of an amplitude sufficient to clear the aperture and then a suitable lateral movement in order not to impede the flow of material. The product obtained exhibited no pollution.

EXAMPLE 2

A crucible of 60 mm diameter consisting of 8 insulated hollow and cooled segments placed inside an inductor supplied with alternating current at a frequency 12 kHz and a power of 60 kW and the bottom of which is provided with an aperture of 8 mm diameter was equipped with an occluding means of a diameter close to that of the aperture, a height of 30 and consisting of two insulated and cooled segments.

In this crucible, 150 g of a mixture of titanium and aluminium in such proportions that they result in the formation of the alloy Ti$_3$Al were melted. The said alloy was then discharged through the bottom in one second, by carrying out the same operations as in Example 1. The product obtained showed no signs of pollution.

The invention finds its application in the processing of materials of high purity which can be recovered conveniently completely and quickly in the liquid state.

We claim:

1. A bottom discharge induction heated crucible formed by a conductive wall (6) consisting of a plurality of longitudinal hollow segments which are at least partially insulated electrically from one another, transversed internally by a cooling fluid and adapted to be placed inside an inductor and in which the said wall is provided in its bottom part with an aperture (3) wherein inside the said aperture is positioned a downwardly removable segmental and cooled occluding means (4) said removable segmental and cooled occluding means including upwardly conical walls and the said plurality of longitudinal hollow segments being upwardly conical.

2. A crucible according to claim 1, wherein the number of segments in the occluding means is less than or equal to the number of segments in the crucible.

3. A crucible according to claim 1, wherein the wall defining said aperture and the occluding means have a complementary upwardly conical shape to facilitate release of the downwardly removable occluding means.

* * * * *